United States Patent [19]

Kessler et al.

[11] Patent Number: 5,753,433
[45] Date of Patent: May 19, 1998

[54] METHOD FOR THE SENSITIVE DETECTION OF NUCLEIC ACIDS

[75] Inventors: Christoph Kessler, Dorfen; Rudiger Ruger, Seehaupt; Rudolf Seibl, Penzberg; Cornelia Kruse-Muller, Tutzing; Sibylle Berner, Augsburg, all of Germany

[73] Assignee: Boehringer Mannheim GmbH, Mannheim, Germany

[21] Appl. No.: 307,414

[22] Filed: Sep. 19, 1994

Related U.S. Application Data

[63] Continuation of Ser. No. 39,010, Apr. 9, 1993, abandoned.

[30] Foreign Application Priority Data

| Dec. 5, 1909 | [DE] | Germany | 40 38 804.2 |
| Oct. 9, 1990 | [DE] | Germany | 40 32 024.3 |
| Dec. 22, 1990 | [DE] | Germany | 40 41 608.9 |

[51] Int. Cl.$^6$ .............. C12Q 1/68; C12Q 1/70; C12P 19/34; C07H 21/04
[52] U.S. Cl. .............. 435/6; 435/5; 435/91.2; 435/174; 536/23.1; 536/26.5; 536/24.3; 536/24.32; 536/24.33
[58] Field of Search .............. 435/6, 5, 91.2, 435/174; 536/23.1, 26.5, 24.3, 24.33

[56] References Cited

U.S. PATENT DOCUMENTS

| 5,200,314 | 4/1993 | Urdea et al. ............... 435/6 |
| 5,232,829 | 8/1993 | Longiam et al. ............... 435/6 |

FOREIGN PATENT DOCUMENTS

| B-21781/88 | 4/1989 | Australia . |
| A-63290/90 | 4/1991 | Australia . |
| A-0297379 | 1/1989 | European Pat. Off. . |
| B-0297379 | 1/1989 | European Pat. Off. . |
| A-0357011 | 3/1990 | European Pat. Off. . |
| A-0361983 | 4/1990 | European Pat. Off. . |
| A-0370694 | 5/1990 | European Pat. Off. . |
| A-0373960 | 6/1990 | European Pat. Off. . |
| A-2202328 | 9/1988 | United Kingdom . |
| WO-9006374 | 6/1990 | WIPO . |
| WO 90/11369 | 10/1990 | WIPO . |
| WO-A-9011374 | 10/1990 | WIPO . |

OTHER PUBLICATIONS

Proc. Natl. Acad. Sci. USA; 87, pp. 1874–1878 (1990) Isothermal, in–vitro amplification of nucleic acids by a multienzyme reaction modeled after retroviral replication.
Proc. Natl. Acad. Sci. USA; 86, pp. 6230–6234 (1989) Genetic analysis of amplified DNA with immobilized sequence–specific oligonucleotide probes.
Proc. Natl. Acad. Sci. USA 86, pp. 1173–1177 (1989) Transcription–based amplification system and detection of amplified human immunomodeficiency virus type 1 with a bead–based sandwich hybridization format.
Innis and Gelfand, in PCR Protocols, A Guide to Methods and Applications, pp. 3–11, Academic Press, 1990.

*Primary Examiner*—Stephanie W. Zitomer
*Assistant Examiner*—Dianne Rees
*Attorney, Agent, or Firm*—Nikaido, Marlmelstein, Murray & Oram LLP

[57] ABSTRACT

Method for the specific detection of nucleic acids in a sample by reaction of the sample with one or several labelled nucleotide triphosphates and one or several enzymes which catalyse the production of a labelled nucleic acid B which contains this nucleotide, non-thermally denaturation, reacting the sample with a nucleic acid probe C which is sufficiently complementary to nucleic acid B and which contains at least one immobilizable group, if desired, contacting the nucleic acid hybrid D formed with a solid phase which recognizes and binds the immobilizable group, removing the liquid from the solid phase and determining the label on the solid phase as a measure for the presence of the nucleic acid.

24 Claims, 6 Drawing Sheets

METHOD FOR THE SENSITIVE DETECTION OF NUCLEIC ACIDS

This application is a continuation division of application Ser. No. 08/039,010 filed Apr. 9, 1993 now abandoned.

The patent application concerns a method for the specific detection of a nucleic acid or a part thereof.

The detection of nucleic acids in clinical diagnostics and in molecular biology has lately increasingly gained in importance over classical immunological tests. This is connected with the progress that has been made with respect to the investigation of the nucleotide sequence of nucleic acids of different origin.

Since the informations embodied in the nucleotide sequence are very discriminating, nucleic acid diagnostics can be used particularly advantageously in order to distinguish the slightest characteristics. This is for example important when testing for mutations and differences in artificially produced sequences. The sensitivity of nucleic acid tests could be considerably increased by the introduction of amplification methods.

Such a method is described for example in EP-A-0 200 362. The amplification effect is mainly based on the fact that by starting with a so-called target nucleic acid as a template and using a primer and mononucleoside triphosphates, an elongation product of the primer is formed which is either detected or can itself again be used as a template nucleic acid. In this process a detectable nucleotide can also be incorporated into the elongation product. The elongation product formed can be detected electrophoretically.

This method of detection is, however, disadvantageous because of the complicated and time-consuming electrophoresis step.

The non-labelled elongation product can also be detected according to EP-A-0 201 184 by hybridization with a detectably labelled nucleic acid probe. However, because of unspecific interactions the separation of the hybrid formed from elongation product and probe from the non-reacted probe using the method described in this application is either inefficient or involves many washing steps which reduce the sensitivity.

A method is proposed in WO 89/11546 in which amplified nucleic acids bound to a solid phase are reacted with a primer and labelled mononucleotides whereby the labelled nucleic acids which are formed in this process are detected. This method has the drawback that all the essential reactions occur on the solid phase which results in an impairment of the reaction rate. Such a method is also proposed in EP-A-0 324 474 in which labelled mononucleotides are incorporated and these labelled nucleic acids are captured by immobilized nucleic acids which are complementary to the nucleic acid to be detected. Nothing is stated about the method used to denature the amplified nucleic acids and the hybridization conditions. A further disadvantage of this method is that the production of nucleic acids which are efficiently bound to a solid phase is complicated.

A method is described in EP-A-0 357 011 in which two primers are used in the elongation reaction of which one is detectably labelled and the other is suitable for binding to a solid phase. This method has the disadvantage that it is more complicated to separate the detectably labelled oligonucleotides from elongation products containing these oligonucleotides. If a separation is not carried out a reduced sensitivity would be expected because of competing reactions.

A method is described in EP-A-0 297 379 and in EP-A-0 348 529 in which an immobilized or immobilizable primer is elongated with a detectable mononucleotide with the aid of the target nucleic acid as template to form an immobilized and at the same time detectably labelled nucleic acid. This method has the disadvantage among others that the specificity of the test is not very high. The method which is also described in EP-A-0 297 379 in which only one immobilized or immobilizable primer is used, whereupon the elongation products are reacted with a labelled oligonucleotide has the disadvantage described in EP-A-0 357 011 that the oligonucleotide is difficult to isolate.

A method is described in WO 89/09281 in which the two primers have the same chemical group which is used, on the one hand, for immobilization and on the other hand for detection. This augments the disadvantage described above of poor separability.

A method is also described in Proc. Natl. Acad. Sci. USA, Vol. 86, pp 6230–6234 in which a detectably labelled primer is elongated. The detection is carried out after binding the elongation product to a capture probe. Also in this case the separation of the detectably labelled primer is not possible without additional steps and it therefore interferes with the detection reaction.

It was therefore the object of the present invention to avoid the drawbacks of the prior art method and in particular to provide a method for the detection of nucleic acids which combines high specificity or selectivity with a low background signal.

The invention concerns a method for the specific detection of a nucleic acid in a sample which comprises the following steps:

a) reacting the sample with one or several labelled mononucleoside triphosphates and one or several enzymes which catalyze the production of a labelled nucleic acid B which contains this nucleotide, b) reacting the sample with a nucleic acid probe C which is sufficiently complementary to the nucleic acid B, c) detecting the nucleic acid hybrid D formed from the labelled nucleic acid B and nucleic acid probe C, d) whereby the nucleic acid probe C contains at least one immobilizable group, e) the reaction mixture is subjected to a non-thermal denaturation after step a), f) the nucleic acid hybrid D is brought into contact with a solid phase which can specifically bind the immobilizable nucleic acid probe C, g) the liquid phase is separated from the solid phase and h) the detectable group bound to the solid phase is detected.

The method according to the present invention is a special way of carrying out the so-called hybridization tests which are known in outline to one skilled in the field of nucleic acid diagnostics. As far as experimental details are not set forth in the following it is referred for full details to "*Nucleic acid hybridisation*", editors B. D. Hames and S. J. Higgins, IRL Press, 1986, in chapters 1 (Hybridisation Strategy), 3 (Quantitative Analysis of Solution Hybridisation) and 4 (Quantitative Filter Hybridisation), *Current Protocols in Molecular Biology*, Edt. F. M. Ausubel, et al., J. Wiley and Son, 1987, 2.9.1–2.9.10 and *Molecular Cloning*, Edt. J. Sambrook et al., Cold Spring Harbor CSH, 1989, 9.4.7.–9.5.8. These include in particular the known methods for the production of labelled nucleoside triphosphates as they are also described in EP-A-0 324 474, the chemical synthesis of modified and unmodified oligonucleotides, the cleavage of nucleic acids by means of restriction enzymes, the selection of hybridization conditions by which a specificity can be achieved which is dependent on the extent of homology between the nucleic acids to be hybridized, their GC content and their length, as well as the formation of nucleic acids from nucleoside triphosphates using polymerases, and if desired, with the use of so-called primers.

A label within the meaning of the present invention consists of a directly or indirectly detectable group L. Directly detectable groups are for example radioactive ($^{32}$p) groups, coloured groups or fluorescent groups or metal atoms. Indirectly detectable groups are for example immunologically or enzymatically active compounds such as antibodies, antigens, haptens or enzymes or enzymatically active partial enzymes. These are detected in a subsequent reaction or reaction sequence. Haptens are particularly preferred since labelled nucleoside triphosphates which are in general particularly good substrates of polymerases can be used with them and a subsequent reaction with a labelled antibody against the hapten or the haptenized nucleoside can be easily carried out. Such nucleoside triphosphates are for example bromo-nucleoside triphosphates or digoxigenin-, digoxin- or fluorescein-coupled nucleoside triphosphates. The steroids mentioned in EP-A-0 324 474 and their detection have proven to be particularly suitable. In this connection reference is made to EP-A-0 324 474 for their incorporation into nucleic acids.

Nucleoside triphosphates (NTP) are ribo (rNTP) or deoxyribonucleoside triphosphates (dNTP).

A target nucleic acid is understood as a nucleic acid which is the target of the detection and starting material for the method according to the present invention.

A template nucleic acid A is a nucleic acid to which a nucleic acid strand which is substantially complementary is formed anew. With respect to the sequence information, the template nucleic acid serves as a template and contains the sequence information which is transcribed in reaction a) into the nucleic acid B. The nucleic acid A is either the target nucleic acid or a nucleic acid derived therefrom. It can for example be a part of the target nucleic acid or contain a part of the target nucleic acid apart from other parts such as highly complex nucleic acids. It can also contain a part of the strand complementary to the target nucleic acid.

Denaturation of nucleic acids means the separation of nucleic acid double strands into single strands. A multitude of variants are available to one skilled in the art.

A specific detection is understood as a method by which, if desired, selectively defined nucleic acids can be detected even in the presence of other nucleic acids. It is, however, also possible to detect several nucleic acids or a group of nucleic acids with a partially identical or similar nucleotide sequence or several sections of a nucleic acid in the presence of other nucleic acids. Either of the two complementary strands can be used to detect double-stranded nucleic acids.

A substantially complementary nucleic acid or nucleic acid sequence is understood as nucleic acids or sequences which can hybridize with the corresponding nucleic acid whose nucleotide sequence is either exactly complementary to the other nucleic acid in the hybridizing region or differs only in a few bases from the exactly complementary nucleic acid. In this connection the specificity depends on the degree of complementarity as well as on the hybridization conditions.

Liquid phases are the aqueous phases usually used in nucleic acid tests with dissolved organic or inorganic constituents e.g. hybridization buffer, excess nucleotides, further nucleic acids which are not to be detected, proteins etc.

The method according to the present invention serves to detect a nucleic acid. In this connection nucleic acids are understood as nucleic acids of any origin, for example nucleic acids of viroid, viral, bacterial or cellular origin. They can be present in solution, suspension, and even immobilized on solids or be present in media containing cells, in cell smears, fixed cells, tissue slices or in fixed organisms. The nucleic acids are preferably present in solution. The reaction sequence is usually started by providing the nucleic acid to be examined with appropriate reagents. In this connection changes in pH (alkaline), heat, repetition of extreme changes in temperature (freezing/thawing), changing the physiological growth conditions (osmotic pressure), the action of detergents, chaotropic salts or enzymes (e.g. proteases, lipases) alone or in combination can contribute to releasing the nucleic acids. Since the method according to the present invention is very sensitive and selective, even small amounts of nucleic acid can be detected in the presence of other materials such as proteins, cells, cell fragments or even nucleic acids which are not to be detected. This therefore obviates a purification of the samples if it can be ensured that the nucleic acids to be detected are sufficiently accessible to the reagents used.

The nucleic acids can also be pretreated. The known pretreatments include in particular fragmentation, for example by means of restriction enzymes, or cDNA synthesis from RNA. In order to fully make use of the advantages of the method according to the present invention it has proven to be expedient that the nucleic acid has a size of at least 40 bp.

In addition the nucleic acid is preferably the product of a prior specific or unspecific nucleic acid amplification. Such nucleic acid amplification methods are known for example from

EP-A-0 201 184, EP-A-0 272 098, DE-A-37 26 934,

EP-A-0 237 362, WO 88/10315, WO 90/01069, WO 87/06270,

EP-A-0 300 796, EP-A-0 310 229, WO 89/09835,

EP-A-0 370 694, EP-A-0 356 021, EP-A-0 373 960,

EP-A-0 379 369, WO 89/12696 or EP-A-0 361 983.

However, the nucleic acid can also be a nucleic acid produced by cloning and in-vivo amplification.

The nucleic acids to be detected (target nucleic acids) can be used directly as template nucleic acids A in reaction a) if they fulfil the requirements necessary for the selected enzyme system. For some enzymes this requires that they are single-stranded nucleic acids, with others it is necessary that they include recognition sites or promoters for the enzyme system.

If this is not the case the target nucleic acids must then be converted into such template nucleic acids A in a step prior to reaction a).

A can be a ribonucleic acid or a deoxyribonucleic acid. Deoxyribonucleic acids are particularly preferred as nucleic acid A.

Within the meaning of the invention the enzyme E is an enzyme or enzyme system which catalyzes the template-dependent synthesis of nucleic acids from mononucleoside triphosphates. Preferred enzymes are polymerases and transcriptases which result in the linkage of mononucleotides. Such enzymes are known to one skilled in the art.

In a first step a labelled nucleic acid B is produced from the template nucleic acid A. This can in principle be carried out in any manner provided that only the specific information of the nucleotide sequence of nucleic acid A or a part thereof is essentially preserved.

A method is for example the exchange of individual nucleotides of nucleic acid A for labelled nucleotides, for example by nick repair (*J. Mol. Biol.* 113, 237 (1977)). In this reaction the enzyme E is *E. coli* DNA polymerase or Kornberg enzyme. This method is, however, not particularly advantageous since the label is introduced relatively unspecifically, i.e. in addition to nucleic acid A all further nucleic acids present in the sample are labelled. It is therefore then especially suitable for reaction a) when, as set forth above, the nucleic acids to be detected have been specifically amplified in a prior amplification reaction.

In another method which also has the above-mentioned disadvantage, the nucleic acid A is elongated (tailing) with incorporation of labelled nucleotides. Further methods of this type are photolabelling and random priming.

In the steps described up to now for the production of nucleic acid B, the target nucleic acid is employed directly in reaction a). This can be present as a single strand or double strand.

The target nucleic acids of the preferred embodiments set out in the following must be made single-stranded before or during reaction a). A separation of the strands which may be necessary can be carried out by treatment with alkali, or even thermally, enzymatically or by means of chaotropic salts.

The use of reactions a) which are dependent on the presence of a specific starter is particularly preferred because of the increased specificity. Such specific starters have the effect that the enzyme only acts on the nucleic acid which has bound this starter. The starter is preferably a so-called specific primer P1, a promoter or a replication initiation region.

Specific primers P1 are especially oligonucleotides or modified oligonucleotides which have a nucleotide sequence which is substantially complementary to the nucleic acid A. Modified oligonucleotides are for example oligonucleotides which contain a dideoxynucleotide at the 3' end. Such oligonucleotides can be produced enzymatically. The target nucleic acid can be used directly as the template nucleic acid A.

The use of such primers P1 therefore requires that at least a part of the sequence of the nucleic acid is known. Moreover, the sequence of the primer is chosen such that one of its ends and preferably the 3' end is shorter than the nucleic acid. This therefore has a single--stranded piece which extends beyond the 3' end of the primer.

In the reaction step one or several specific primers can be used per nucleic acid single strand to be detected. In the case of several primers, it is preferred that the regions on the nucleic acid with which the primers can hybridize do not overlap and particularly preferably there are single-stranded regions of the nucleic acid A between these regions. Apart from a part which is substantially complementary to the nucleic acid A the primer can also include a nucleotide sequence S1, preferably at the 5' end, which cannot hybridize with the nucleic acid, in particular in the region which is adjacent to the complementary region.

This sequence S1 can for example be single-stranded or double-stranded and can also contain a recognition sequence for an enzyme. This can e.g. be a restriction cleavage site. With regard to an effective priming the primer can also contain for example a bound protein which is recognized by an enzyme E, preferably a polymerase.

In order that the reaction a) can proceed, the nucleic acid A and the primer P1 must each at first be separated in the complementary region from complementary strands which may be present. This separation can be carried out by known methods for example thermally or non-thermally. The non-thermal denaturation is preferred. Reaction a) is then started under conditions in which A and P1 can hybridize with one another.

When a primer is used as starter, an enzyme E which can synthesize complementary nucleic acids to A in a primer-dependent reaction is also added to the sample. This in particular includes polymerases. Their substrate specificity depends on the nucleic acid A. If A is RNA then especially RNA-dependent DNA polymerases such as reverse transcriptase (e.g. from AMV or M-MuLV) come into consideration. If A is DNA then DNA-dependent DNA polymerases such as Klenow enzyme of the taq DNA polymerase is preferred.

Deoxyribonucleoside triphosphates (dNTP) are also added to the sample of which at least one is labelled.

The product of the polymerase reaction is a labelled deoxyribonucleic acid B in which the primer P1 as well as the labelled deoxyribonucleoside triphosphate are incorporated. This nucleic acid B is of the same size or smaller than the template, but has a region of which at least a part is substantially complementary to the template.

This nucleic acid B can now be used directly in step b). However, it is advantageous to subject it once again as a template nucleic acid to a reaction analogous to step a). For this a primer P2 is added to the sample which is substantially complementary to a part of the nucleic acid B, preferably to a part of the region newly formed from dNTPs. The primer pair P1 and P2 preferably fulfil the conditions described in EP-A-0 201 184. P1 and P2 are preferably added simultaneously to the template A.

In order to achieve an even higher sensitivity it is possible to carry out reaction a) several more times, preferably 1–60, particularly preferably 20–60 times whereby the products of the reaction are each used again in reaction a). This results theoretically in an almost exponential multiplication of labelled nucleic acids. In this process both nucleic acid strands are formed whereby the length is determined by the non-extendable ends of the primers P1 and P2. It is also possible in analogy to EP-A-0 201 184 to use so-called nested primers in the later passages of reaction a) whose sequence is selected such that the nucleic acids which are formed are smaller than those formed at first. Before each passage of reaction a) it is expedient to separate the double strands formed from A and B in reaction a). This can be carried out thermally or non-thermally. In each case primers P1 and P2 have to again be present.

The starter can also be a promoter. A promoter is a nucleotide sequence which is recognized by a RNA polymerase and which causes this to synthesize a nucleic acid strand B complementary to the nucleotide sequence which follows the promoter. In this process the labelled NTP is also incorporated into the nucleic acid strand formed in addition to the non-labelled NTPs.

Suitable promoters are known, for example RNA polymerase binding sites from bacteriophages such as T3, T7 or SP6 (Melton et al.: NAR 12, 1984, 7035–56; Pfeiffer & Gilbert: *Protein Sequences and DNA-Analysis I*, 1988, 269–280; Uhlenbeck et al.: Nature 328, 1987, 596–600).

In a preferred embodiment of the method of detection the promoter is part of a specific primer for the production of the template nucleic acid A from the target nucleic acid. This primer has a nucleotide sequence S1 which is substantially complementary to a part of the target nucleic acid and a nucleotide sequence S2 which is recognized by a RNA polymerase and includes at least a promoter sequence. In a first reaction a nucleic acid strand A1 which is at least partially complementary to the target nucleic acid and includes the primer with the promoter is formed using the primer, a DNA polymerase which is dependent on the type of target nucleic acid and dNTPs. If it is not already linked to the primer the newly formed piece of nucleic acid is covalently linked to the primer by addition of a further enzyme which is preferably a ligase e.g. E. coli DNA ligase. The ligase can also be thermally stable. A1 is preferably shorter than the target nucleic acid.

In this transcription reaction a second primer P3 which is complementary to the target nucleic acid strand is preferably used and the gap between the two primers is closed for example by a gap filling reaction. In this case the use of labelled dNTPs is not yet necessary since this step would only lead to a slight amplification of the measured signal in the method according to the present invention but it is possible.

If the target nucleic acid is RNA then this is preferably selectively degraded in a subsequent step. Known methods are suitable for this, for example treatment with alkali or with RNAses. Subsequently a nucleic acid strand A2 which is complementary to A1 is formed. For this a primer P2 is added to the reaction mixture which is complementary to a part, preferably to a newly formed part, of the strand A1. The primer P2 preferably also contains the promoter sequence S2. This is elongated to A2 as described above for A1. Such steps in the process are e.g. described in EP-A-0 329 822, DE-A-37 26 934, WO 88/10315, WO 87/06270, EP-A-0 310 229 and EP-A-0 373 960 which is why references are made in full detail to these disclosures. In particular the reader is referred to this disclosure with regard to details which are helpful and necessary for the reverse transcription of RNA or the transcription of DNA.

In this embodiment it is particularly preferred that the sample additionally contains the complementary strand to the target nucleic acid whereby P1 and P2 are elgonated simultaneously.

In the said embodiment a promoter-specifically controlled DNA-dependent RNA polymerase is subsequently added to the sample pretreated in this way. Such polymerases are e.g. T3, T7 or SP6 RNA polymerase. Using these, labelled nucleic acids B are formed from NTPs and the labelled NTP. The double-stranded nucleic acid A1/A2 serves in this case as a template nucleic acid, preferably several times.

Preferred NTPs are ribonucleoside triphosphates. Since in this variant of reaction a) single-stranded nucleic acids B are formed, a denaturation in order to separate the strands is not absolutely necessary but possible.

A preferred embodiment is the procedure according to DE-A-4010465 U.S. patent application Ser. No. 07/676,695 but using detectably labelled ribonucleoside triphosphates.

The starter is preferably a replication initiation region (RIR). A replication initiation region is, for example, a nucleotide sequence which is recognized by a replication enzyme or replication enzyme complex, for example a DNA-dependent polymerase such as from φ 29 (P2, P3). It is particularly preferred that the RIR is part of a specific primer. This primer has a nucleotide sequence S1 which is substantially complementary to a part of the target nucleic acid and adjacent to this a sequence S2 which has a recognition site, preferably proteins, for a replication complex. Such a primer is denoted adapter Ad in the following. The reaction is started by reacting the target nucleic acid which is actually the species to be detected with Ad under hybridization conditions. It is particularly preferred to use two adaptors Ad1 and Ad2 per target nucleic acid single strand whereby the target-specific sequences can hybridize with spaced-apart sequences of the single-stranded target nucleic acid and the target-specific sequences of the adaptors are directed towards each other on the target nucleic acid.

The single-stranded gap between the adaptors is filled in with a gap filling reaction (Maniatis et al., *Molecular Cloning*, 1982, Cold Spring Harbor). The use of labelled NTPs is not necessary but possible. As a result a nucleic acid double strand is formed which contains one strand of the target nucleic acid and one strand of the newly formed nucleic acid A. This contains at least one, preferably two, replication initiation regions which are particularly preferably arranged in opposite directions of replication.

From this double strand a labelled nucleic acid B can be produced in a manner according to the present invention by replication without further addition of adaptors and using labelled and unlabelled nucleoside triphosphates in reaction a). This in turn contains at least one, preferably two, replication initiation regions and can therefore again be employed in reaction a) as a template nucleic acid. Thus a considerable amplification of B is achieved. In the case that both adaptors each have one RIR or that two nucleic acids A which are complementary to one another are used in reaction a), two nucleic acids B can form which are complementary to one another. These must be separated from one another before step b) by denaturation.

After step a) the reaction mixture is subjected to a non-thermal denaturation (reaction e)) in the method according to the present invention. Also if step a) is carried out several times the non-thermal denaturation takes place directly before step b). In particular nucleic acid double strands are separated from one another in this process. Non-thermal denaturation denotes that the temperature for the denaturation is not above 50° C., preferably not above 37° C. and preferably takes place in a range between 22 and 37° C. In the denaturation, nucleic acid double strands which may be present are separated from one another so that nucleic acid B is present as a single strand. This can for example be carried out by changing the stringency and also by enzymes, for example helicase, recA protein, *E. coli* ssb protein, gene-32 protein and by alkali or by addition of double strand stabilizing chemicals such as e.g. organic substances such as urea, formamide (concentration >70%, *NAR* 1977, Vol. 4, 5, 1539–1553) or chaotropic salts. Chaotropic salts are described in *J. Biol. Chem.* 1966, 241/17, 4030–4042, *J. Amer. Chem. Soc. USA* 1962, 84/8, 1329–1338 or *Anal. Biochem.* 129, 357–364 (1983). NaI, guanidinium thiocyanate or NaClO$_4$ are particularly preferred within the scope of the invention. The concentration of these salts necessary for denaturation can be determined by simple experiments. However, they are e.g. for NaI preferably ca.12.2 mol/l, for guanidinium salts ca.4 mol/l and for NaClO$_4$ ca.7 mol/l.

Alkaline denaturation has proven to be particularly advantageous in this case. For this the reaction mixture from reaction a) is adjusted to a pH in the range of 10 to 14, preferably of 12 to 14. This can for example be carried out by addition of a solution of NaOH or KOH in water.

The temperature of the mixture during the incubation of 1 to 30 min and preferably of 5 to 10 min is in a range of 17° to 50° C., preferably of 22° to 37° C.

In the following reaction step b) nucleic acid B is made to react with the probe C in such a way that they together form a nucleic acid hybrid D.

As nucleic acid probe C oligonucleotides or polynucleotides with a length of 6 to 5000, preferably 15 to 2000 come in particular into consideration. The probe C can be a plasmid, a nucleic acid fragment or an oligonucleotide. It can be RNA or DNA. Nucleic acid probe C is added to the reaction mixture in excess of the expected amount of nucleic acid B and is preferably in the form of an aqueous solution. The probe C has a nucleotide sequence which is substantially complementary to B and is specific for B, thus it does not hybridize or only to a very slight extent with nucleic acids present in the sample or newly formed nucleic acids which are not intended to be detected. By combining the use of specific primers with hybridization with a specific probe the method according to the present invention becomes particularly selective.

C can be a double-stranded nucleic acid, one of whose strands C1 is complementary to a part of B. The other strand C2 of the nucleic acid probe is preferably complementary to other nucleic acids B, in particular to those which are formed during the course of reaction a) with B as template nucleic acid. The denaturation of C can in this case be carried out separately from B. It is however, preferable to denature C together with B. This is in particular the case for alkaline denaturation. For this C is preferably added to the reaction mixture from a) before the alkalisation. After an incubation period the mixture is adjusted to a pH of 5.0 to 8.5, preferably 7–8, whereupon the nucleic acid hybrids D are formed from B and C1 or C2.

The case is preferred in which C is a single-stranded nucleic acid probe C1 and the strand C2 complementary to C1 is not added. Even then it is still possible to add C1 before the denaturation of B. However, in the case of the alkaline denaturation of B it is particularly preferable first to only incubate B in alkali and then to add an acidic solution of the probe C1. The pH of the acidic solution of C1 is in a range from 3.0 to 6.5, preferably 4.5 to 6.0, without there being evidence of a noticeable instability of the probe. The weakly acidic solution should be adequate to adjust the pH from 5.0 to 8.0 after addition of the hybridization solution. The solution may also be buffered in this range and contain further reagents which aid in the hybridization such as e.g. SSC, formamide or blocking reagents for nucleic acids which are not to be detected. The pH of the mixture after addition of C1 should also in this case be in the range from 5.0 to 8.5. The fine regulation of the pH can for example be carried out via the amount of hybridization solution as well as by its pH.

Acids which can be used for neutralisation or as a component of the hybridization solution are for example hydrochloric acid or formic acid; however, acetic acid or phosphoric acid are preferred. The pH of the hybridization solution before addition of the sample is between 3.0 and 6.5. The concentration of the acetic acid as an example is preferably between 0.05 and 0.5 mol/l, particularly preferably between 0.1 and 0.2 mol/l.

Single-stranded nucleic acid probes C1 can for example be produced by chemical nucleic acid synthesis according to DE-A-39 16 871 or also according to EP-B-0 184 056.

This embodiment has the advantage that by using the probe solution to neutralise the sample solution it is possible to dispense with a pipetting step. In addition it has turned out that the addition of a concentrated acid to the alkali treated sample which has a high protein content leads to disadvantageous agglomerations. The use of diluted acids with the above described acidities is particularly advantageous as their use prevents such agglomerations from forming.

If a denaturation by means of double-stranded destabilizing substances has been carried out before step b) then the conditions for the hybridization with the probe C can be adjusted by diluting the mixture. Probe C contains one or several (immobilizable) groups I per nucleic acid strand which are capable of immobilizing.

Groups I capable of immobilization are for example chemical groups which can be covalently bound to a solid phase for example via a chemical or a photoreaction, or groups or parts of molecules which can be recognized and bound by another molecule or part of a molecule via group-specific interactions. Such groups are therefore e.g. haptens, antigens and antibodies, nucleotide sequences, receptors, regulation sequences, glycoproteins, for example lectins, or even the binding partners of binding proteins such as biotin or iminobiotin. Vitamins and haptens are preferred, biotin, fluorescein or steroids such as digoxigenin or digoxin are particularly preferred. It is important for the invention that in each hybrid D the immobilizable group of the probe differs from the detectable group of the nucleic acid B.

The mixture, which contains the nucleic acid hybrid D if the nucleic acid to be detected was present in the sample, is subsequently brought into contact with a solid phase F which can specifically bind the hybrid D via the immobilizable groups of the nucleic acid probe C.

The type of solid phase depends on the group I which is capable of immobilization. It preferably has an immobilizing group R which can participate in a binding interaction with I. If the immobilizable group is for example a hapten then a solid phase can be used which has antibodies against this hapten on its surface. If the immobilizable group is a vitamin such as e.g. biotin then the solid phase can contain immobilized binding proteins such as avidin or streptavidin. Particularly preferred residues I and R are biotin and streptavidin. Immobilization via a group on the modified nucleic acid is particularly advantageous since it can take place under milder conditions than for example hybridization reactions.

In order to immobilize the nucleic acids formed it is preferred that after formation of the nucleic acid hybrids D the reaction mixture is poured into a vessel which can react with the immobilizable group at its surface. The hybridization reaction with the probe preferably takes place at the same time as the immobilization. The vessel can for example be a cuvette, a tube or a microtitre plate. It is, however, also possible to use a solid phase in the form of a porous material such as a membrane, a fabric or a pad onto which the reaction mixture is applied. It is also possible to use so-called beads or latex particles. The solid phase should at least have as many binding sites for the immobilizable group of the probe as the number of nucleic acid hybrids D and thus nucleic acids B which are present.

The production of a preferred solid phase is described in EP-A-0 344 578 U.S. patent application Ser. No. 07/356,336, filed May 24, 1989, abandoned in favor of U.S. patent application Ser. No. 07/691,685, filed on Apr. 25, 1991, abandoned in favor of U.S. patent application Ser. No. 07/925,300, filed Aug. 5, 1992 which is referred to in full detail.

After an incubation period during which the immobilization reaction takes place, the liquid phase is removed from the vessel, the porous material or the pelleted beads. The solid phase can subsequently be washed with a suitable buffer since the binding of the hybrids D to the solid phase is very efficient. The method according to the present invention allows particularly few washing steps to be used in this process since in contrast to the detectable probes used in the state of the art it is not absolutely necessary to completely remove the difficultly separable probes, or it leads to comparatively small background signals.

The amount of modified nucleic acids bound to the solid phase can in principle be determined in a known way whereby the steps which have to be carried out depend on the type of the detectable group. In the case of directly detectable groups such as fluorescent labels, the amount of label is determined fluorometrically. If the detectable group is a hapten then the modified nucleic acid is preferably reacted with a labelled antibody against the hapten analogous to the description in EP-A-0 324 474. The label can for example be an enzyme label, such as β-galactosidase, alkaline phosphatase or peroxidase. In the case of an enzyme label, the amount of nucleic acid is measured by means of the usually photometric, chemoluminometric or fluorometric monitoring of a reaction of the enzyme with a chromogenic, chemoluminogenic or fluorogenic substrate. It is, however, also possible to monitor the reaction electrochemically if a redox enzyme is used as the label, or to monitor a change in pH by means of a pH electrode. The measured signal is a measure of the amount of target nucleic acid originally present.

The detection of the nucleic acid can be carried out qualitatively as well as quantitatively. In the case of a quantitative evaluation it has turned out to be expedient to carry out at least one comparative experiment with a sample of known nucleic acid content. It is possible and recommended that a calibration curve be constructed.

In one embodiment of the method using PCR, oligonucleotides are added to the sample as primers P1 and P2. In this case P1 is complementary to a part of the nucleic acid single strand A which simultaneously represents the target and the template nucleic acid. P2 is homologous to a part of A which is at a distance therefrom. The mixture is now treated as described in EP-A-0 201 184 whereby however, apart from the unmodified deoxymononucleotide triphosphates a digoxigenin-labelled or fluorescein-labelled deoxymononucleotide triphosphate is also used. Preferably 20 to 30 amplification cycles are carried out. Afterwards double-stranded biotin-labelled probe C and sodium hydroxide solution are added to a pH of 10–14. The mixture is incubated at ca. 37° C. and subsequently a solution of hybridization auxiliary substances are added at ca. pH 5 so that a pH of ca. 7–8.5 results. The mixture is transferred to a streptavidin-coated vessel and again incubated. The solution is removed and the vessel washed. A conjugate of antibody against digoxigenin and an enzyme is added and it is incubated again. After removing the solution and washing the vessel, it is reacted with a chromogenic substrate of the enzyme and the formation of colour is observed.

A preferred embodiment is a variant of the replication method described in DE-A-39 29 030 (U.S. patent application Ser. No. 07/835,446). The disclosure of DE-A-39 29 030 is hereby referred to in full detail. In order to carry out the method the sample, which contains the single-stranded target nucleic acid, is mixed with two adaptors which are complementary to the same strand and whose ends, which hybridize with A, are orientated towards one another and whose non-hybridizing ends contain a replication initiation sequence for φ 29 polymerase. Under hybridization conditions the gap between the adaptors is closed by gap filling using DNA polymerase or reverse transcriptase (as enzyme E1) and a ligase reaction. The deoxymononucleoside triphosphates used for this can be unmodified, however, it is preferable that one of them is a digoxigenin-labelled monodeoxyribonucleoside triphosphate. In order to carry out the replication, the replication system of φ 29 (P2, P3 and ATP) as well as a digoxigenin- or fluorescein-labelled monodeoxyribonucleoside triphosphate are added in addition to unmodified mononucleoside triphosphates if they have not already been used for the gap filling reaction. The detectably-labelled nucleic acids B which are formed by replication serve anew as template nucleic acids without further addition of adaptors to form further nucleic acids B. In the course of time this theoretically leads to an exponential amplification of the detectably-labelled nucleic acids B.

As soon as sufficient nucleic acids have been formed, the mixture is subjected to a non-thermal denaturation step and a preferably single-stranded biotin-labelled probe C1 is added in a solution containing hybridization reagents at pH 3.0–6.5 up to a pH of 5.0–8.5, preferably 7.0–8.0. By introducing the non-thermal denaturation step it is possible to carry out the entire test procedure in a temperature range between 17 and 50° C. and preferably at a single temperature. The mixture is transferred to a streptavidin-coated vessel and incubated. After aspirating the liquid and washing the vessel, a solution of a conjugate of an enzyme-labelled antibody against digoxigenin or fluoroscein is added and it is again incubated. After aspirating the solution and washing, a solution of a chromogenic substrate is added and the formation of color is observed.

In state of the art methods detectably-labelled probes have always been used up to now. A complete separation of the non-hybridizing probes was necessary for the accuracy of the measurement results but it was relatively complicated.

The method according to the present invention obviates this disadvantage by measuring the presence of incorporated labelled mononucleotides and using this as a measure for the presence or the amount of nucleic acids to be detected instead of hybridizing and determining labelled probes. The separation of non-incorporated labelled mononucleotides can be particularly simply and completely achieved according to the present method since they are neither bound to the nucleic acids nor to the surface. An excess of immobilizable probe C on the other hand does not interfere with the determination since the immobilizable groups of probe C are not used as a label and thus cannot contribute to the measured result. In particular the binding capacity of the solid phase can be more easily calculated than when incorporating immobilizable NTPs.

The method according to the present invention is therefore very sensitive and selective and in addition it can be carried out in a very short time.

The method according to the present invention is suitable for the detection of nucleic acids as such, of organisms containing nucleic acids such as bacteria, viruses and cells and for the detection of alterations in nucleic acids such as mutations or chromosome translocations and for locating genes and determining their degree of expression. Ribonucleic acids as well as deoxyribonucleic acids can be detected. It is also possible to identify selective differences in nucleic acids when the results of experiments are compared in which a primer is used in reaction a) which is complementary to the nucleic acid A at its 3' end and on the other hand a primer is used which is not complementary to nucleic acid A at its 3' end but nevertheless hybridizes with it. An elongation of the primer and thus the formation of nucleic acid B is only possible in the first case. The choice of such primers is described for example in PNAS 86, 2757 (1980).

Figure 1:
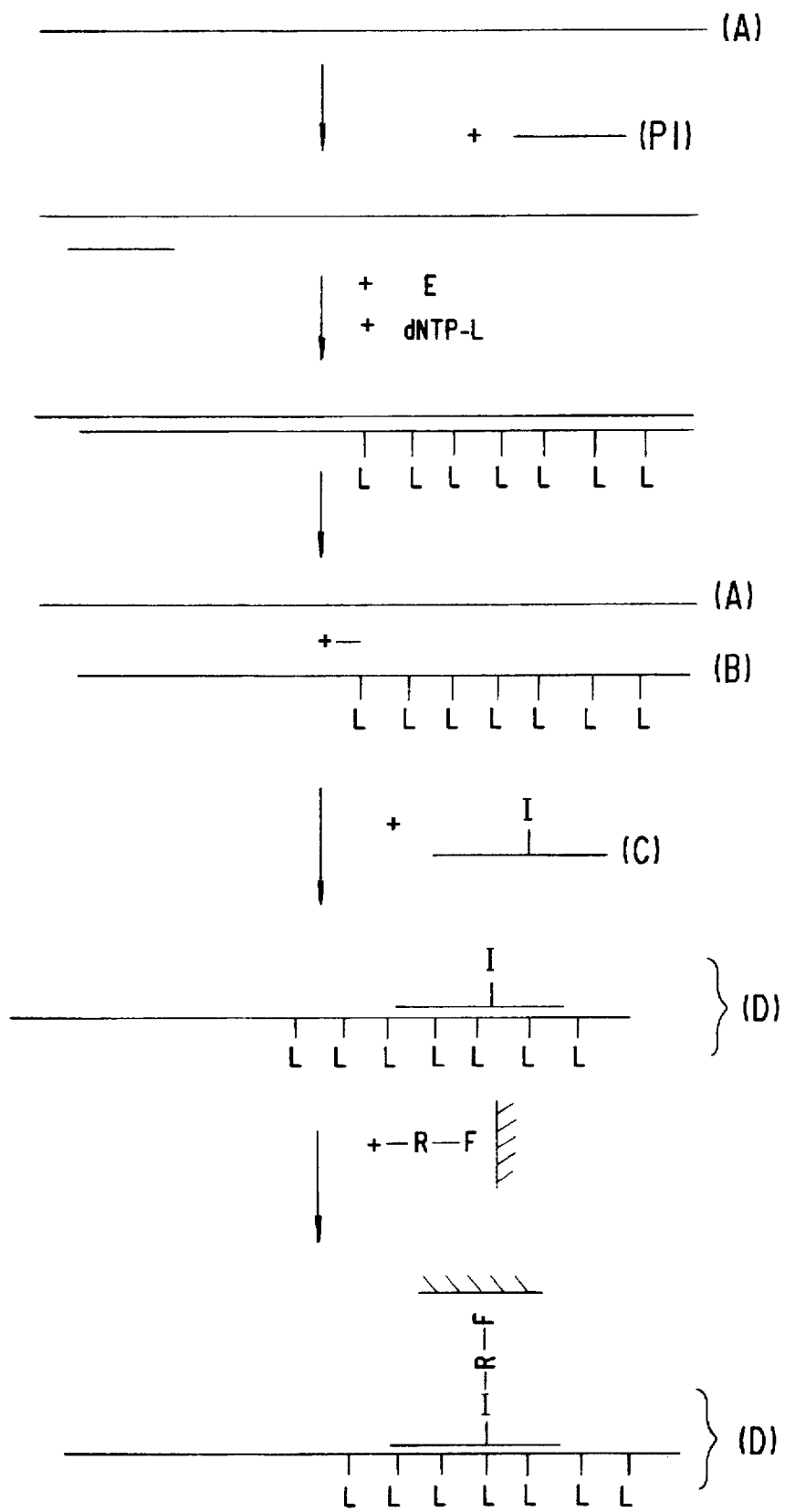
FIG. 1 shows a diagram of the course of an embodiment using a primer elongation (use of only one primer P1).
Figure 2:
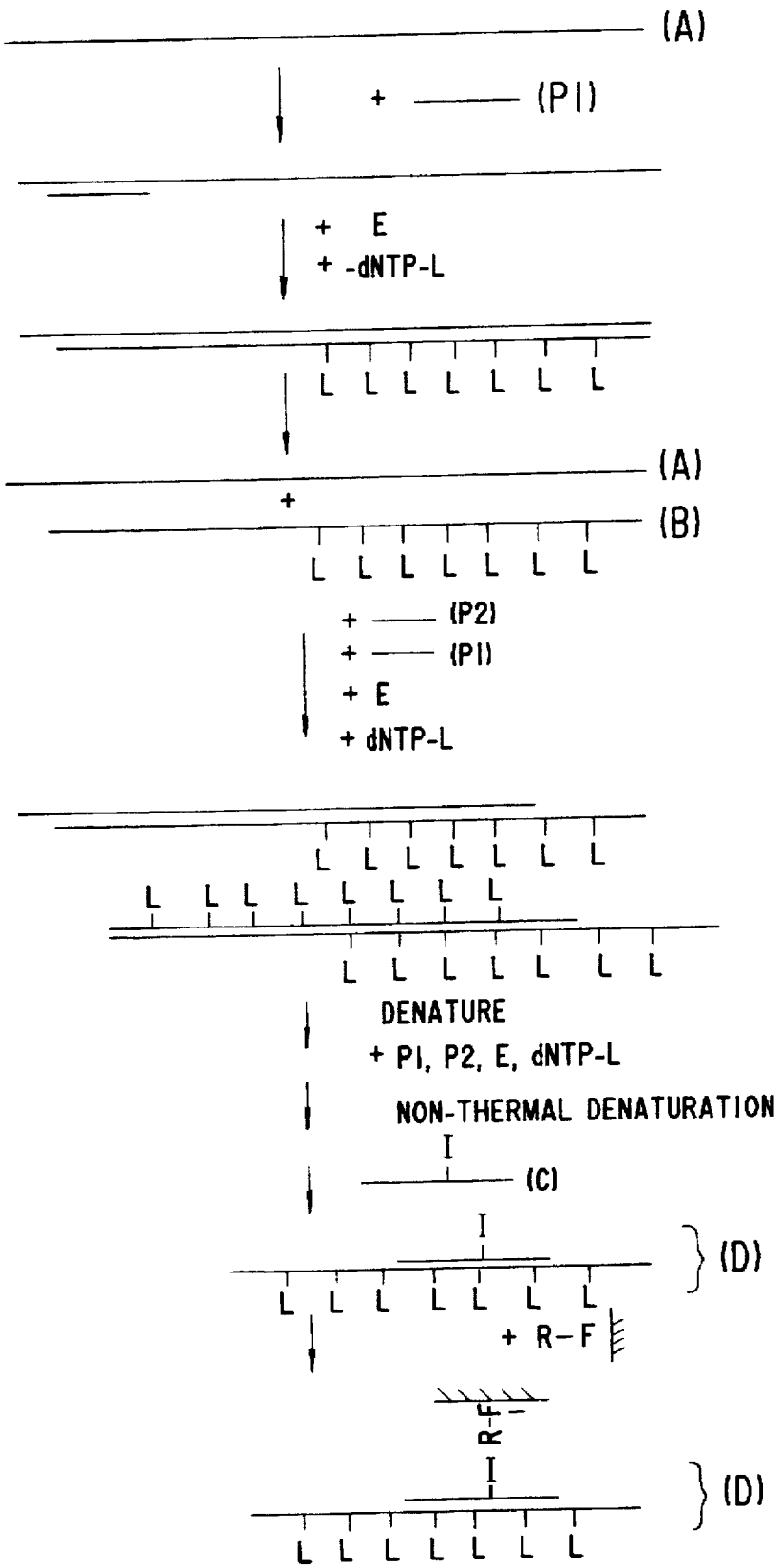
FIG. 2 shows a diagram of the course of an embodiment using the PCR principle with two primers in which the nucleic acids B which are formed at first are again used as template nucleic acid.
Figure 3:
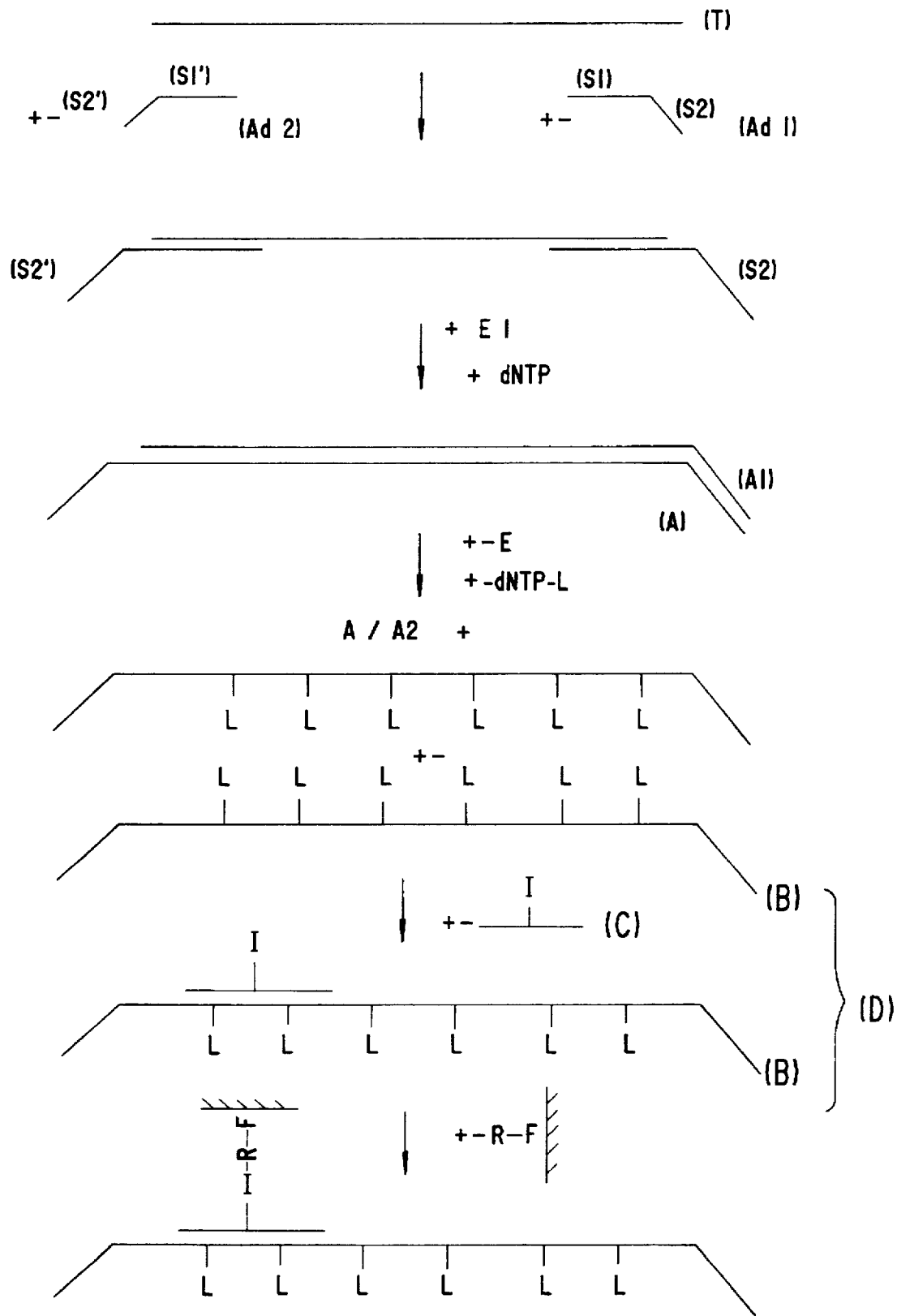
FIG. 3 shows a diagram of the course of the preferred embodiment using a replication amplification.

REFERENCE SYMBOLS:

A template nucleic acid
A1 opposite strand of A
P1 primer complementary to A
E enzyme/enzyme complex
E1 DNA polymerase or reverse transcriptase
L detectable group (label)
B product of reaction a)
C nucleic acid probe
I immobilizable group
D nucleic acid hybrid from B and C
R immobilizing group
F solid phase
S1 sequence complementary to A
S1' another sequence complementary to A
S2 promoter or first replication initiation sequence (origin of replication)
S2' promoter or second replication initiation sequence (origin of replication)
Ad1 adaptor 1, complementary to the target nucleic acid
Ad2 adaptor 2, complementary to the target nucleic acid The invention is elucidated further by the following examples.

EXAMPLE 1

Amplification of the target DNA using a detectably-labelled deoxyribonucleoside triphosphate (step a))

The polymerase chain reaction is carried out with cloned HBV-specific sequences. The primers used bind to position 1937–1960 and 2434–2460 in the HBV genome, i.e a sequence of 523 nucleotides is amplified (R. Sumazaki, et al., 1989, J. Med. Virol. 27, 304–308). The concentration of the DNA to be amplified in the plasmid corresponds to 100 ag to 100 pg in the dilution series used in this case. 30 PCR cycles (2 min 92° C.; 2 min 50° C.; 2 min 70° C.) are carried out in 100 μl with primers each at a concentration of 200 nM; 50 mM KCl, 10 mM Tris-HCl pH 8.5, 1.5 mM MgCl₂, 100 μg/ml gelatin; 200 μm dATP, 200 μm dCTP, 200 μm dGTP, 150 μm dTTP, 50 μm digoxigenin-11-2'-deoxy-uridine-5'-dUTP (DIG-[11]-dUTP, Boehringer Mannheim), 2.5 U *Thermus aguaticus* (Taq) DNA polymerase.

Non-thermal denaturation (step e))

20 μl of this mixture after PCR and 40 ng biotin-labelled sample DNA (random primed, cloned HBV DNA between position 27 and 2604, double-stranded) are denatured in a total volume of 44 μl in 0.5M NaOH for 10 min at 37° C. Hybridization with probe C (step b)) and solid phase binding (step f))

Subsequently it is neutralized by addition of 156 μl hybridization solution at pH 5 and it is pipetted into a streptavidin-coated microtitre plate (hybridization solution= 62.5 mM sodium phosphate, 6.25×SSC [1×SSC =NaCl, 0.15M; sodium citrate, 0.015M] and formamide 62.5%). The hybridization reaction/wall-binding reaction is carried out for 18 hours at 37° C. while gently shaking.

Detection of the hybrid D (steps c), g) and h))

After removing the liquid and washing 5×with 0.025% NaCl and 1 oo/o (0.1%) copper sulphate, 200 mU/ml anti-digoxigenin-horseradish peroxidase conjugate is added and incubated for 60 min at 37° C. in 10 mM Tris-HCl, pH 7.5; 0.9% NaCl, 1% BSA, 0.5%

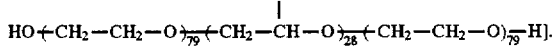

PLURONIC F68 [poloxamer, $$HO\text{+}CH_2\text{—}CH_2\text{—}O\text{)}_{\overline{79}}\text{+}CH_2\text{—}CH\text{—}O\text{)}_{\overline{28}}\text{+}CH_2\text{—}CH_2\text{—}O\text{)}_{\overline{79}}H].$$

After washing 5 times (conditions the same as above) it is incubated with 0.1% 2,2-azino-di-[3-ethylbenzthiazol]-(ABTS) for 60 min at 37° C. and the absorbance is measured at 405 nm.

Figure 4:
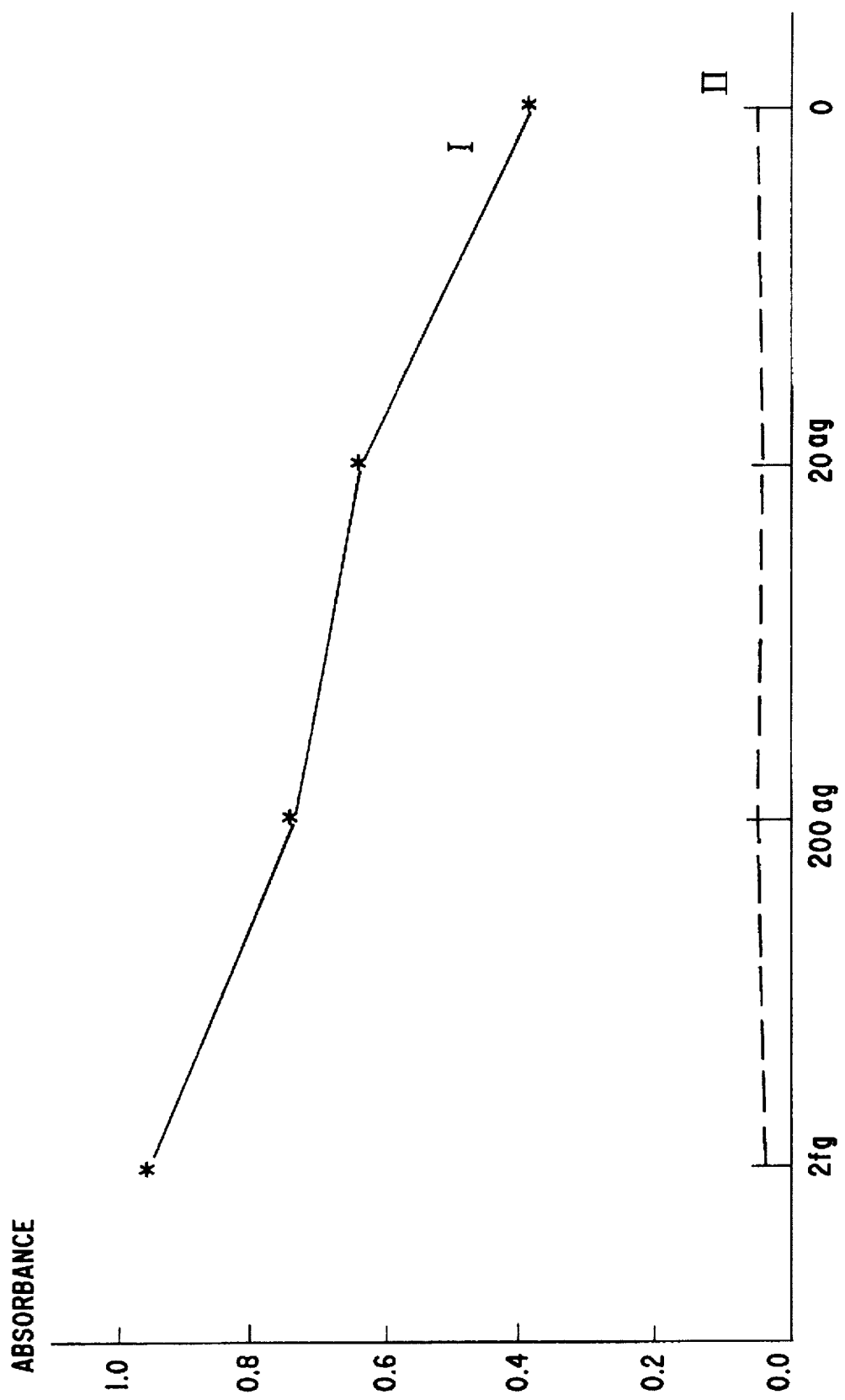
FIG. 4 shows the result of an experiment according to FIG. 1 in curve I. The absorbance measured in the solution is plotted against the amount of nucleic acid A to be detected; curve II shows the result in the absence of the nucleic acid to be detected.

The absorbances for this reaction and for the control reactions with bio-labelled sample are shown in FIG. 4.

EXAMPLE 2

The amplification reaction (polymerase chain reaction) is carried out with control serum (HBV DNA negative) which is enriched with HBV-specific DNA. A 523 bp long DNA fragment is formed in the amplification because of the position of the selected PCR primer (PCR primer 1: position 1937–1960, PCR-primer 2: position 2434–2460 in the HBV genome, see Example 1 for literature). A dilution series is made from this plasmid in a range of 10 pg/ml to 1.25 pg/ml in control serum. In relation to the DNA region of the plasmid to be amplified, this corresponds to amounts in the range of 40 ag to 320 ag DNA which are used in the amplification reaction. 50 μl 10 mM Tris-HCl (pH 8.3) and 20 μl 0.5N NaOH are added to 10 μl of the control serum supplemented with plasmid-DNA for the alkaline lysis and incubated for 1 h at 37° C. 10 μl of the lysis preparation are used in the amplification reaction after neutralizing with 20 μl 0.5N HCl. The reaction is carried out in a total volume of 100 μl with 200 nM of each of the PCR primers, 200 μM DATP, dCTP and dGTP in each case, 175 μM dTTP, 25 μM digoxigenin-11-2'-dUTP (Boehringer Mannheim), 2.5 U *Thermus aquaticus* DNA polymerase, 50 mM KCl, 10 mM Tris-HCl (pH 8.3), 1.5 mM MgCl₂, 0.01% gelatin. After overlayering the solution with 100 μl mineral oil it is incubated in a thermocycler (Perkin Elmer): 30 sec 92° C., 30 sec 50° C., 60 sec 70° C., 30 cycles in all. After completion of the amplification 10 μl 0.5N NaOH is added to 40 μl of the preparation and incubated for 10 min at room temperature. It is neutralized by addition of 450 μl hybridization solution (50 mM Na phosphate buffer, 0.75M NaCl, 0.075M Na citrate, 0.05N HCl, 0.05% BSA, pH 5.4) to which 220 ng/ml biotin-labelled oligonucleotide (Bio-Oli 25, biotin-labelled according to Applied Biosystems, User Bulletin, DNA Synthesizer No. 49, 1988, position 2327–2356 in the HBV genome), which is complementary to a region of the amplified DNA region is added. 200 μl of the hybridization preparation is incubated for 3 h at 37° C. in a well of a streptavidin-coated microtitre plate. After aspirating the solution it is subsequently washed 2×10 min at 37° C. with 0.3M NaCl, 0.03M Na citrate, 0.2% SDS and 1×for a short time at room temperature with 0.9% NaCl. 200 mU/ml anti-digoxigenin antibody-horseradish peroxidase conjugate in 100 mM Tris-HCl (pH 7.5), 0.9% NaCl, 1% BSA are added and incubated for 30 min at 37° C. After washing 3 times with 0.9% NaCl the substrate solution (1.9 mM ABTS$^R$) is added and the absorbance is measured at 405 nm.

Figure 5:
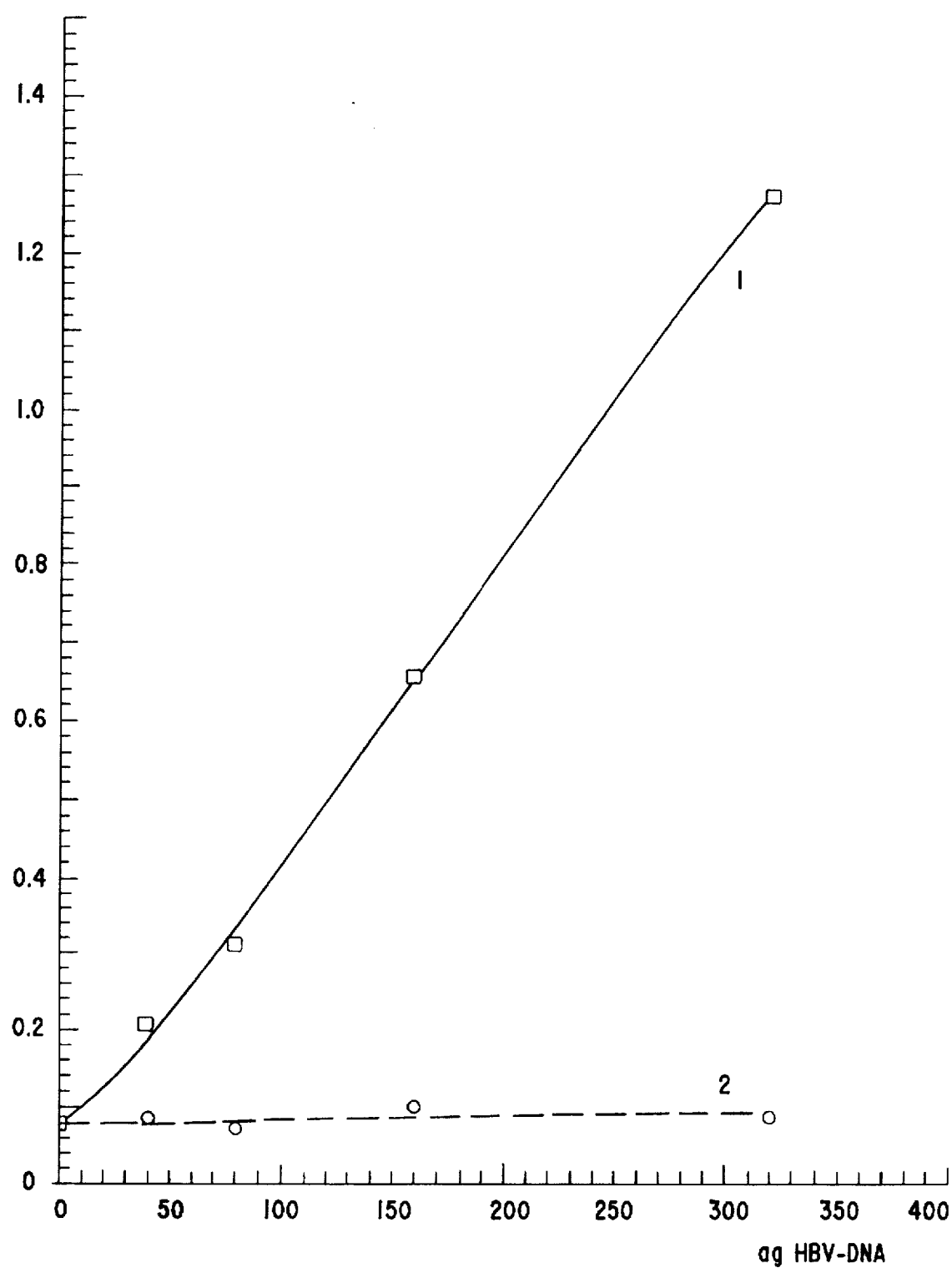
FIG. 5 shows a calibration curve 1 for a determination of HBV DNA by means of PCR and a single-stranded biotin-labelled oligonucleotide according to Example 2. Curve 2 shows the blank value (without addition of Bio-Oli 25).

The results of the reaction are shown diagramatically in FIG. 5.

EXAMPLE 3

HBe-positive human plasma with a virus titre of 1×10^10 Hepatitis B viruses per mol is diluted in normal serum so that the virus content in the dilutions is between $0.25×10^5$/ml to $2×10^5$/ml. In order to lyse the viruses 10 µl 0.2 NaOH is added to 10 µl of the serum dilution and incubated for 1 h at 37° C. Subsequently it is neutralized by adding 30 µl neutralization solution (100 mM KCl, 20 mM Tris-HCl (pH 8.3)), 3 mM $MgCl_2$, 0.02% gelatin to 10 µl of the lysis preparation. The reaction is carried out in a total volume of 100 µl with 200 nM of each of the two PCR primers, 200 µM dATP, dCTP and dGTP, 175 µM dTTP, 25 µM digoxigenin-11-2'-dUTP (Boehringer Mannheim), 50 mM KCl, 10 mM Tris-HCl (pH 8.3), 1.5 mM $MgCl_2$, 0.01% gelatin, 2.5 U Thermus aquaticus DNA polymerase. The reaction preparation is overlayered with 100 Al mineral oil and incubated in a thermocycler (Perkin Elmer) 30 cycles: 30 sec at 92° C., 30 sec at 50° C. and 1 min at 70° C.

Figure 6:
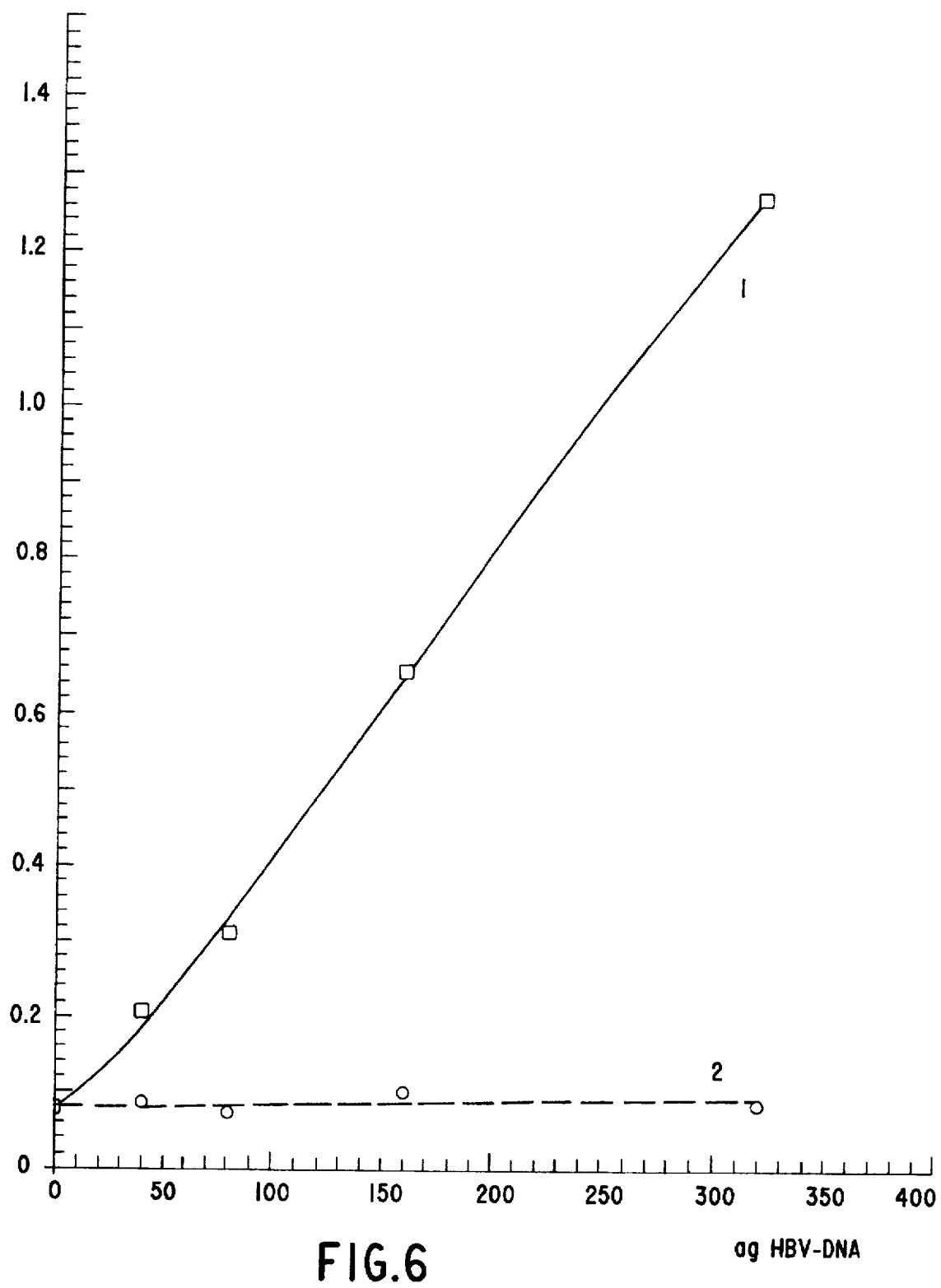
FIG. 6 shows a calibration curve 3 for the determination of HBV in a method according to Example 3. Curve 4 shows the blank value (without addition of Bio-Oli 25).

A 523 bp DNA fragment is produced by the amplification step (HBV PCR primer 1: position 1937–1960, HBV PCR primer 2: position 2434–2460 in the HBV genome). The specific detection of the PCR products is carried out in a two-component test system on the solid phase. 20 µl TE buffer (10 mM Tris-HCl (pH 7.5) 1 mM EDTA) and 10 µl 0.5N NaOH are first added to 20 µl of the amplification mixture and incubated for 10 min at room temperature. It is neutralized by addition of 450 µl acidified hybridization solution (50 mM Na phosphate buffer, 0.05N HCl, 0.75M NaCl, 0.075M Na citrate, 0.05% BSA, pH 5.4) to which 100 ng/ml of a biotin-labelled oligonucleotide is added which corresponds to a region of the amplified DNA region (HBV biotin oligonucleotide, 30 mer, twice biotin-labelled, position 2327–2356 in the HBV genome, Bio-Oli 25, produced by solid-phase synthesis, labelled with biotin as described in Example 2). 200 µl of this hybridization preparation is incubated in a well of a streptavidin-coated microtitre plate for 3 h at 37° C. while shaking. After the hybridization reaction and wall-binding reaction the solution is aspirated and washed 2×10 min with 0.3M NaCl, 0.03M Na citrate, 0.2% SDS at 37° C. and 1×0.9% NaCl for a short time at room temperature. After addition of 200 mU/ml anti-digoxigenin antibody-horseradish peroxidase conjugate in 100 mM Tris-HCl (pH 7.5), 0.9% NaCl, 1% BSA it is incubated for 30 min at 37° C. while shaking. Unbound conjugate is removed by washing three times with 0.9% NaCl at room temperature. After incubating for 30 minutes with 1.9 mM $ABTS^R$ (2,2'-azino-di-[3-ethyl-benzthiazoline-sulfonic acid (6)]-diammonium salt) at 37° C. the absorbance is measured at 405 nm using an ELISA reader. The results are shown in FIG. 6.

We claim:

1. A method for the specific detection of a nucleic acid in a sample comprising the steps of:
    a) first reacting the sample with at least one labelled mononucleoside triphosphate and at least one enzyme which catalyzes the production of a labelled nucleic acid B, which contains said labelled mononucleoside triphosphate, to form a reaction mixture; wherein said sample is reacted in the presence of a primer P1, which is sufficiently complementary to a part of a template nucleic acid to hybridize specifically to said part of the template nucleic acid and is elongated by the enzyme to form said nucleic acid B which incorporates the labelled mononucleoside triphosphate and which is sufficiently complementary to at least part of the template nucleic acid to hybridize specifically to the template nucleic acid,
    b) then non-thermally denaturing any nucleic acids in the reaction mixture,
    c) then hybridizing the nucleic acid B with a nucleic acid probe C which contains at least one immobilizable group and which is sufficiently complementary to the nucleic acid B to hybridize specifically with nucleic acid B,
    d) immobilizing the nucleic acid probe C on a solid phase,
    e) then separating the solid phase from the reaction mixture, and
    f) thereafter detecting a nucleic acid hybrid D formed from the labelled nucleic acid B and nucleic acid probe C by detecting any labeled nucleic acid bound to the solid phase, wherein steps c) and d) are performed simultaneously and wherein said immobilizable group is different from the label on said labelled mononucleoside triphosphate.

2. Method according to claim 1, further comprising adding primer P2 which is sufficiently complementary to a part of the nucleic acid B to hybridize specifically to the nucleic acid B.

3. Method according to claim 2, wherein nucleic acids are formed by elongation of the primers P1 and P2, and are again reacted with P1 and P2 after strand separation whereby the nucleic acids formed serve as a template for the elongation of one primer by using the other primer.

4. Method according to claim 1, wherein the enzyme catalyses polymerization of said mononucleoside triphosphates to form a nucleic acid B which is sufficiently complementary to a nucleic acid to be detected, to hybridize specifically to the nucleic acid to be detected.

5. Method according to claim 4, wherein the mononucleoside triphosphates are ribonucleoside triphosphates.

6. Method according to claim 4, wherein the mononucleoside triphosphates are deoxyribonucleoside triphosphates.

7. Method according to claim 1, wherein the nucleic acid to be detected is single-stranded or is made single-stranded.

8. The method according to claim 7, further comprising adding at least one adaptor containing 1) a nucleotide sequence which is sufficiently complementary to a part of the template nucleic acid to be detected to hybridize specifically to the template nucleic acid, and 2) a replication initiation region, to the sample per single strand to be detected, wherein the adaptor hybridizes to the template nucleic acid and is elongated by a sequence which is complementary to the nucleic acid using a polymerase or a gap filling reaction and the nucleic acid thus formed is used as a template nucleic acid in reaction a) for the production of nucleic acid B.

9. Method according to claim 7, further comprising adding at least one primer containing a nucleotide sequence which is sufficiently complementary to a part of the nucleic acid to be detected to hybridize specifically to the nucleic acid to be detected and containing a transcription initiation sequence, to the sample per single strand to be detected, wherein the primer hybridizes to the nucleic acid to be detected and is elongated by a nucleotide sequence which is complementary to the nucleic acid using a polymerase or a gap filling reaction and the nucleic acid thus formed is used as a template nucleic acid in reaction a) for the production of nucleic acid B.

10. Method according to claim 1, wherein the nucleic acid B formed in step a) is used as a template nucleic acid in step a) for the production of additional nucleic acids.

11. Method according to claim 1, wherein step a) is carried out several times in succession and the products of step a) serve as starting materials for the next step a).

12. Method according to claim 10, wherein a nucleic acid hybrid is formed in step a) from a nucleic acid in said sample and nucleic acid B.

13. Method according to claim 1, wherein step B takes place at an alkaline pH.

14. Method according to claim 13, wherein the nucleic acid probe C is added in a solution with a pH between 10 and 14 and subsequently the reaction mixture is adjusted with a hybridization solution to a pH between 5.0 and 8.5.

15. Method according to claim 13, wherein a solution of the nucleic acid probe C is first combined with the sample, then adjusted to a pH between 10 and 14 and subsequently the pH in the mixture is adjusted to between 5.0 and 8.5.

16. Method according to claim 1, wherein step b) is carried out by addition of chaotropic salts.

17. Method according to claim 1, wherein step b) is carried out at a temperature range of between 17° C. and 50° C.

18. Method according to claim 1, wherein the method takes place at a temperature range of between 17° C. and 50° C.

19. Method according to claim 18, wherein the method takes place at a single temperature.

20. Method according to claim 1, wherein the nucleic acid probe C is added at a pH between 3.0 and 6.5.

21. Method according to claim 20, wherein nucleic acid probe C is in a solution which contains all the reagents necessary for carrying out the hybridization.

22. Method according to claim 1, wherein the nucleic acid probe C is a single-stranded nucleic acid C whose opposite strand is absent from the solution.

23. A method for specifically detecting a nucleic acid in a sample comprising the steps of:

a) adding mononucleoside triphosphates and at least one enzyme which catalyzes the production of a nucleic acid B by incorporating said mononucleoside triphosphates, to the sample to form a reaction mixture, wherein at least one of the mononucleoside triphosphates is detectably labelled, b) thereafter denaturing any nucleic acids in the reaction mixture, c) then hybridizing the nucleic acid B with a nucleic acid probe C which contains at least one immobilizable group, d) immobilizing the nucleic acid probe C on a solid phase, e) separating the reaction mixture from the solid phase, and f) detecting any labeled nucleic acid bound to the solid phase, wherein steps c) and d) are performed simultaneously.

24. The method according to claim 1, wherein steps b)–f) are performed in a single reaction vessel.

* * * * *

UNITED STATES PATENT AND TRADEMARK OFFICE
CERTIFICATE OF CORRECTION

PATENT NO. : 5,753,433

DATED : May 19, 1998

INVENTOR(S) : Kessler et al.

It is certified that error appears in the above-identified patent and that said Letters Patent is hereby corrected as shown below:

```
On the title page,
    Item [30], line 1, please delete "Dec. 5, 1909" insert therefor -- Dec. 5, 1990 --.
```

Signed and Sealed this

Twenty-first Day of July, 1998

*Attest:*

BRUCE LEHMAN

*Attesting Officer*   *Commissioner of Patents and Trademarks*